United States Patent [19]

Craven, III

[11] Patent Number: Plant 6,411

[45] Date of Patent: Nov. 22, 1988

[54] *MYRICA CERIFERA* VAR. PUMILA NAMED 'GEORGIA GEM'

[75] Inventor: William H. Craven, III, Waynesboro, Ga.

[73] Assignee: Twisted Oaks Nursery, Waynesboro, Ga.

[21] Appl. No.: 929,321

[22] Filed: Nov. 10, 1986

[51] Int. Cl.[4] ..... A01H 5/00

[52] U.S. Cl. ..... Plt./54

[58] Field of Search ..... Plt./54, 88

[56] References Cited

PUBLICATIONS

Gray, A "Myricaceae Wax-Myrtle Family" *Gray's Manual of Botany* 8th ed. 1950, American Book Co., N.Y. pp. 524 and 525 only.

*Primary Examiner*—James R. Feyrer

*Attorney, Agent, or Firm*—Charles W. Rummler

[57] ABSTRACT

A new and distinct variety of dwarf southern waxmyrtle distinguished by its compact production of branches and leaves spaced from 35 to 65 mm. apart along the ground-parallel stem and the overall tightness of branching growth; its rich light yellow-green leaves that mature to dark olive green, which are smaller than those of the species, and which grown from more closely spaced nodes thereby producing a much denser foliage. The plant is an evergreen shrub that will withstand temperatures as low as 0° F., it has full sun or partial shade tolerance and the average linear growth of the main stem is approximately six inches per year.

BACKGROUND OF THE NEW PLANT

My new *Myrica cerifera* var. pumila originated at my nursery at Waynesboro, Georgia, in the spring of 1983 as an aberant plant type found in a group of 150 seedlings planted at my nursery from seeds resulting from open pollination of a particularly compact form of dwarf southern waxmyrtle and the selection of this new variety was made by reason of the distinctive characteristics that were displayed by this unusual plant and which represented a new and improved combination of characteristics never before exhibited in any *Myrica cerifera* var. pumila of which I am aware.

Among the outstanding characteristics of this new variety, which distinguish it from other varieties of *Myrica cerifera* var. pumila and all other Myrica species, are a compact, broad spreading, suckering mound habit with an ultimate size approximately 12 to 18 inches in height and 30 to 36 inches in width, as well as rich, light yellow-green leaves that mature to dark olive green and are quite smaller than the species, and more closely spaced nodes and thus denser foliage with good tolerance of full sun and partial shade, all of which were retained by my asexual propagation of the discovery plant by cuttings and thereafter conducted through several successive generations, which demonstrated clearly that the novel characteristics of this new variety would hold true from generation to generation and appeared to be firmly fixed.

2 Drawing Sheets

---

DESCRIPTION OF THE DRAWING

My new variety of *Myrica cerifera* var. pumila is illustrated by the accompanying drawings which, in full color, show in FIG. 1, a view of a row of the new plants growing from a single, ground-parallel stem.

DESCRIPTION OF THE NEW PLANT

Figure 1:
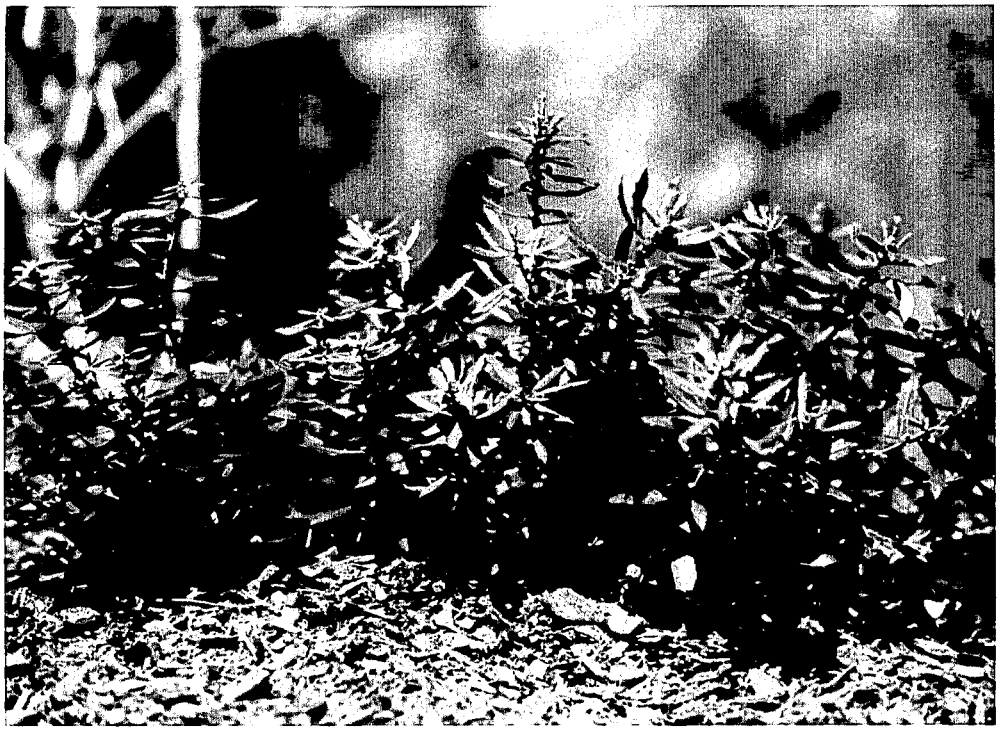
Figure 2:
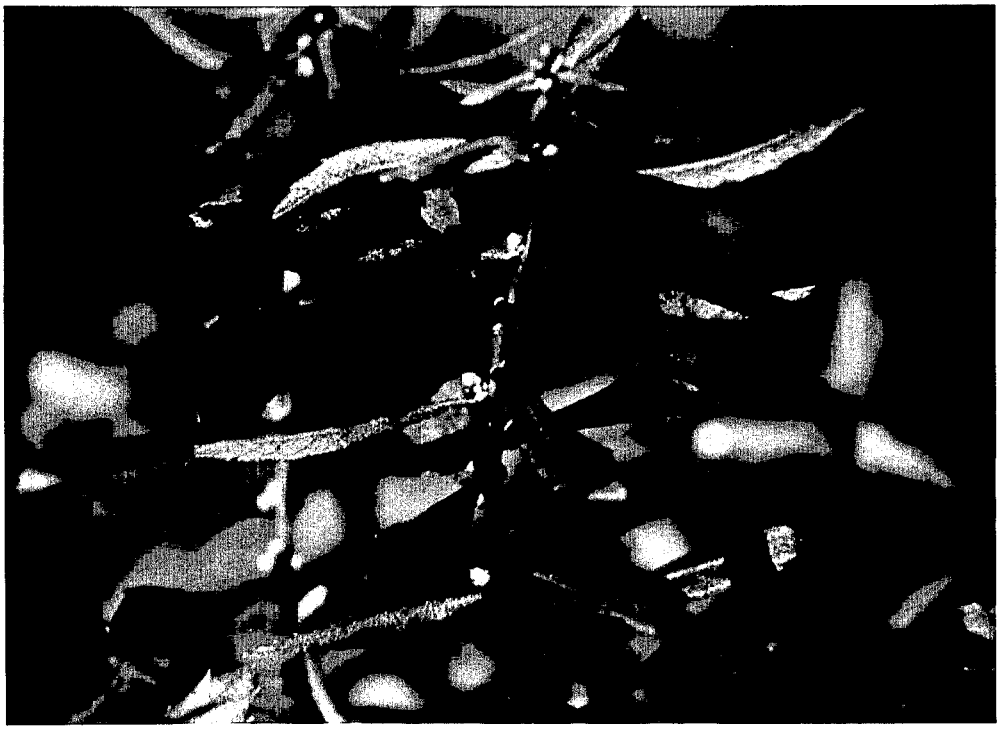
in FIG. 2, a close-up view of one of the branches growing vertically from the main horizontal stem and showing buds and leaves; and in FIG. 3, a hand-made drawing showing a branch of the new variety and front and back side views of a single leaf, the colors shown being as close to those herein specified as it is reasonably possible to obtain by conventional photographic procedures.
Figure 3:
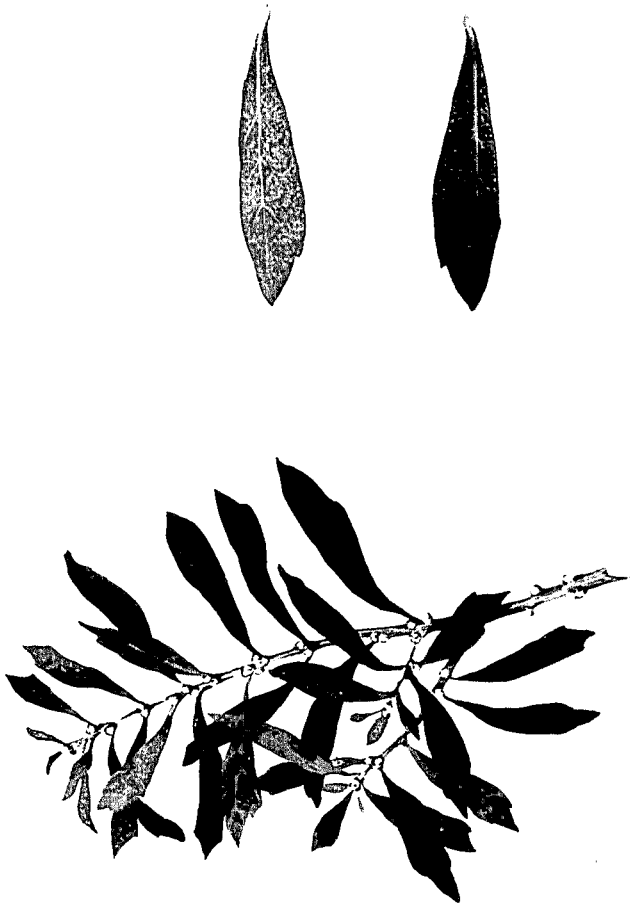

The following is a detailed description of my new variety of *Myrica cerifera* var. pumila as observed in 1986 from plants grown at my nursery in Waynesboro, Ga., with color designations according to The H.C.C. Colour Chart published in 1941 by The Royal Horticultural Society of London, England, with collaboration of The British Colour Council.

THE PLANT

Form: Broadleaf evergreen shrub.

Shape: Upright branches, closely spaced along a horizontal main stem, each densely clothed with foliage.

Height: Approximately 12 to 18 inches.

Main stem:

*Length.*—About 30 to 36 inches.

Growth: Compact, with broad spreading, suckering mound habit with a slow to moderate main stem growth rate, averaging about 6 inches per year.

Branching character: Slender, upright stems growing from closely spaced nodes about $\frac{1}{8}$ to $\frac{1}{4}$ inch apart along the main stem.

Foliage:

*Quantity.*—Abundant.

*Size of leaf.*—About $\frac{3}{4}$ to $1\frac{1}{2}$ inches long and about $\frac{1}{4}$ to $\frac{3}{8}$ inches wide, growing alternately along the upright stem.

*Leaf shape.*—Linear with acute tip and entire margins except that in the upper one-third of the leaf length, the margins have irregularly spaced serrations.

*Texture.*—Leathery.

*Aspect.*—Both surfaces covered with numerous, minute, yellowish-brown resin glands.

*Ribs and veins.*—A prominent, yellow-green midvein and no secondary veins visible to the naked eye.

Petiole.—Length: About 1/16 to ⅛ inch. Color: New leaves are yellow-green when emerging, HCC Pod Green 061, or Lettuce Green 861/2; color changing to Olive Green at maturity HCC 0960/2. Time of color change dependent on climatic conditions. In Waynesboro, Ga., growth is more-or-less continuous from June to August; the yellow-green color of new growth being transitional with the Olive Green mature foliage.

THE BUD

Size: Small, about 1/16 inch long.

Shape: Ovoid to rounded.

Color: Light green, with scales covered with yellowish-brown resin glands.

Borne: The buds sit in axils of leaves and form a 45° angle with the stem.

THE FLOWER

The flowers of this new variety are similar in color but are smaller than those of a normal *Myrica cerifera* var. pumila which have yellowish-green flowers with male and female flowers usually occurring on separate plants (dioecious). The sex of the new variety appears to be both male and female.

THE FRUIT

To date, the parent plant has not fruited. The small, 1/10 to ¼ inch diameter, grayish, waxy coated drupes occur only on female plants of the species. The sex of this new variety is unknown.

For this new variety, such resistance is excellent. *Myrica cerifera* var. pumila displays excellent tolerance in insects and diseases and the present plant has been completely free of disease for more than four years that I have observed and grown it. Also, the new variety has not been eaten by rabbits or deer.

My new variety of *Myrica cerifera* var. pumila, which I call 'Georgia Gem', is particularly distinguished by its smaller leaves than the parent species, which have leaves much larger and up to about 1 to 3 inches long; and by the more closely-spaced nodes on the main stem and thus denser foliage. This new variety will withstand temperatures as low as 0° F. and its leaves are cold hardy to 0° F. with the stems withstanding temperatures to minus 5° F. Also, the new variety is full sun or partial shade tolerant and is easy to root from cuttings in August to October, which assures trueness to type.

This new variety also has a distinct bayberry candle fragrance to leaves and stems that is especially evident in large, mass plantings.

I claim:

1. A new and distinct variety of dwarf southern waxymyrtle, *Myrica cerifera* var. pumila, as herein shown and described, particularly characterized by its compact, broad spreading, suckering, mounded habit with small, dainty, olive-green leaves that are very closely spaced along the upright stems creating a dense foliage mass; an evergreen constitution with foliage maintaining, olive-green color in cold weather; and with a particular adaptability to dry, sandy soils, with full sun to partial shade tolerance.

* * * * *